US009731133B1

(12) United States Patent
Thacker et al.

(10) Patent No.: US 9,731,133 B1
(45) Date of Patent: Aug. 15, 2017

(54) SYSTEMS AND METHODS FOR SYSTEMATICALLY TESTING A PLURALITY OF THERAPY PROGRAMS IN PATIENT THERAPY DEVICES

(71) Applicant: Nevro Corporation, Menlo Park, CA (US)

(72) Inventors: James R. Thacker, Homer, AK (US); Jon Parker, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 28 days.

(21) Appl. No.: 14/161,512

(22) Filed: Jan. 22, 2014

Related U.S. Application Data

(60) Provisional application No. 61/755,380, filed on Jan. 22, 2013.

(51) Int. Cl.
*A61N 1/36* (2006.01)

(52) U.S. Cl.
CPC ..... *A61N 1/36132* (2013.01); *A61N 1/36071* (2013.01)

(58) Field of Classification Search
CPC ............ A61N 1/36146; A61N 1/36185; A61N 1/36132; A61N 1/36071
See application file for complete search history.

(56) References Cited

U.S. PATENT DOCUMENTS

| | | |
|---|---|---|
| 4,019,519 A | 4/1977 | Geerling |
| 4,210,151 A | 7/1980 | Keller, Jr. |
| 4,257,429 A | 3/1981 | Dickhudt et al. |
| 4,340,063 A | 7/1982 | Maurer |
| 4,467,800 A | 8/1984 | Zytkovicz |
| 4,899,750 A | 2/1990 | Ekwall |
| 5,016,635 A | 5/1991 | Graupe |

(Continued)

FOREIGN PATENT DOCUMENTS

| | | |
|---|---|---|
| EP | 1331965 A2 | 8/2003 |
| JP | 08503648 | 4/1996 |

(Continued)

OTHER PUBLICATIONS

Hayt et al., "Engine Circuit Analysis," McGraw-Hill Book Company, Fourth Edition, 1986, 18 pages.

(Continued)

*Primary Examiner* — William Levicky
(74) *Attorney, Agent, or Firm* — Perkins Coie LLP

(57) ABSTRACT

Methods for systematically testing a plurality of therapy programs in a spinal cord modulation system, and associated systems are disclosed. A representative method comprises loading a plurality of therapy programs into a signal generator, wherein individual therapy programs include parameters specifying electrode configuration, signal amplitude, and/or signal frequency. The programs are automatically activated for an automatically instructed period of time. The method includes automatically changing from one therapy program to another after the instructed period of time. The patient is queried for patient input corresponding to the therapy programs. The patient input is received via a remote. The patient input is correlated with a corresponding time of day and recorded in the signal generator. Thereafter, the patient input is retrieved from the signal generator.

25 Claims, 3 Drawing Sheets

(56) References Cited

U.S. PATENT DOCUMENTS

| | | |
|---|---|---|
| 5,031,618 A | 7/1991 | Mullett |
| 5,063,929 A | 11/1991 | Bartelt et al. |
| 5,069,211 A | 12/1991 | Bartelt et al. |
| 5,143,081 A | 9/1992 | Young et al. |
| 5,159,926 A | 11/1992 | Ljungstroem |
| 5,184,617 A | 2/1993 | Harris et al. |
| 5,222,494 A | 6/1993 | Baker, Jr. |
| 5,335,657 A | 8/1994 | Terry, Jr. et al. |
| 5,342,409 A | 8/1994 | Mullett |
| 5,354,320 A | 10/1994 | Schaldach et al. |
| 5,423,329 A | 6/1995 | Ergas |
| 5,540,730 A | 7/1996 | Terry, Jr. et al. |
| 5,641,326 A | 6/1997 | Adams |
| 5,643,330 A | 7/1997 | Holsheimer et al. |
| 5,702,429 A | 12/1997 | King |
| 5,782,884 A | 7/1998 | Stotts et al. |
| 5,814,092 A | 9/1998 | King |
| 5,843,146 A | 12/1998 | Cross, Jr. |
| 5,891,179 A | 4/1999 | Er et al. |
| 5,913,882 A | 6/1999 | King |
| 5,938,690 A | 8/1999 | Law |
| 6,052,624 A | 4/2000 | Mann |
| 6,155,267 A | 12/2000 | Nelson |
| 6,208,894 B1 | 3/2001 | Schulman et al. |
| 6,236,892 B1 | 5/2001 | Feler |
| 6,308,102 B1 | 10/2001 | Sieracki et al. |
| 6,341,236 B1 | 1/2002 | Osorio et al. |
| 6,353,762 B1 | 3/2002 | Baudino et al. |
| 6,381,496 B1 | 4/2002 | Meadows et al. |
| 6,393,325 B1 | 5/2002 | Mann et al. |
| 6,393,328 B1 | 5/2002 | McGraw et al. |
| 6,440,090 B1 | 8/2002 | Schallhorn |
| 6,461,357 B1 | 10/2002 | Sharkey et al. |
| 6,516,227 B1 | 2/2003 | Meadows et al. |
| 6,574,507 B1 | 6/2003 | Bonnet |
| 6,587,727 B2 | 7/2003 | Osorio et al. |
| 6,609,030 B1 | 8/2003 | Rezai et al. |
| 6,609,032 B1 | 8/2003 | Woods et al. |
| 6,622,048 B1 | 9/2003 | Mann et al. |
| 6,659,968 B1 | 12/2003 | McClure |
| 6,671,556 B2 | 12/2003 | Osorio et al. |
| 6,740,072 B2 | 5/2004 | Starkweather et al. |
| 6,803,102 B1 | 10/2004 | Talley et al. |
| 6,873,872 B2 | 3/2005 | Gluckman et al. |
| 6,895,280 B2 | 5/2005 | Meadows et al. |
| 6,909,917 B2 | 6/2005 | Woods et al. |
| 6,920,357 B2 | 7/2005 | Osorio et al. |
| 6,947,792 B2 | 9/2005 | Ben-Haim et al. |
| 6,950,707 B2 | 9/2005 | Whitehurst |
| 6,961,618 B2 | 11/2005 | Osorio et al. |
| 6,978,171 B2 | 12/2005 | Goetz et al. |
| 7,010,345 B2 | 3/2006 | Hill et al. |
| 7,020,523 B1 | 3/2006 | Lu et al. |
| 7,024,246 B2 | 4/2006 | Acosta et al. |
| 7,024,247 B2 | 4/2006 | Gliner et al. |
| 7,050,856 B2 | 5/2006 | Stypulkowski |
| 7,110,821 B1 | 9/2006 | Ross |
| 7,123,967 B2 | 10/2006 | Weinberg |
| 7,127,296 B2 | 10/2006 | Bradley |
| 7,142,923 B2 | 11/2006 | North et al. |
| 7,174,215 B2 | 2/2007 | Bradley |
| 7,184,837 B2 | 2/2007 | Goetz |
| 7,191,012 B2 | 3/2007 | Boveja et al. |
| 7,206,632 B2 | 4/2007 | King |
| 7,239,920 B1 | 7/2007 | Thacker et al. |
| 7,239,926 B2 | 7/2007 | Goetz |
| 7,242,984 B2 | 7/2007 | DiLorenzo |
| 7,252,090 B2 | 8/2007 | Goetz |
| 7,263,402 B2 | 8/2007 | Thacker et al. |
| 7,266,412 B2 | 9/2007 | Stypulkowski |
| 7,286,878 B2 | 10/2007 | Stypulkowski |
| 7,289,851 B2 | 10/2007 | Gunderson et al. |
| 7,295,876 B1 | 11/2007 | Erickson |
| 7,317,948 B1 | 1/2008 | King et al. |
| 7,343,200 B2 | 3/2008 | Litvak et al. |
| 7,349,739 B2 | 3/2008 | Harry et al. |
| 7,403,821 B2 | 7/2008 | Haugland et al. |
| 7,406,351 B2 | 7/2008 | Wesselink |
| 7,444,181 B2 | 10/2008 | Shi et al. |
| 7,447,545 B2 | 11/2008 | Heruth et al. |
| 7,450,992 B1 | 11/2008 | Cameron |
| 7,463,927 B1 | 12/2008 | Chaouat |
| 7,483,747 B2 | 1/2009 | Gliner et al. |
| 7,489,970 B2 | 2/2009 | Lee et al. |
| 7,555,346 B1 | 6/2009 | Woods et al. |
| 7,571,001 B2 | 8/2009 | Thacker et al. |
| 7,603,175 B2 | 10/2009 | Voelkel |
| 7,617,002 B2 | 11/2009 | Goetz |
| 7,634,315 B2 | 12/2009 | Cholette |
| 7,647,101 B2 | 1/2010 | Libbus et al. |
| 7,657,317 B2 | 2/2010 | Thacker et al. |
| 7,660,628 B2 | 2/2010 | Libbus et al. |
| 7,706,889 B2 | 4/2010 | Gerber et al. |
| 7,747,330 B2 | 6/2010 | Nolan et al. |
| 7,751,900 B2 | 7/2010 | Voelkel |
| 7,783,349 B2 | 8/2010 | Libbus et al. |
| 7,799,021 B2 | 9/2010 | Leung et al. |
| 7,801,601 B2 | 9/2010 | Maschino et al. |
| 7,801,619 B2 | 9/2010 | Gerber et al. |
| 7,801,621 B1 | 9/2010 | Thacker et al. |
| 7,819,909 B2 | 10/2010 | Goetz et al. |
| 7,831,305 B2 | 11/2010 | Gliner |
| 7,831,307 B1 | 11/2010 | Moffitt |
| 7,853,322 B2 | 12/2010 | Bourget et al. |
| 7,853,323 B2 | 12/2010 | Goetz |
| 7,872,884 B2 | 1/2011 | Parramon et al. |
| 7,873,418 B2 | 1/2011 | Stypulkowski |
| 7,881,805 B2 | 2/2011 | Bradley et al. |
| 7,945,330 B2 | 5/2011 | Gliner et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,966,073 B2 | 6/2011 | Pless et al. |
| 8,016,776 B2 | 9/2011 | Bourget et al. |
| 8,095,220 B2 | 1/2012 | Lee et al. |
| 8,116,878 B1 | 2/2012 | Palmer |
| 8,121,703 B1 | 2/2012 | Palmer |
| 8,170,675 B2 | 5/2012 | Alataris et al. |
| 8,175,719 B2 | 5/2012 | Shi et al. |
| 8,311,639 B2 | 11/2012 | Parker et al. |
| 8,355,797 B2 | 1/2013 | Caparso et al. |
| 8,457,759 B2 | 6/2013 | Parker et al. |
| 8,498,710 B2 | 7/2013 | Walker et al. |
| 8,626,312 B2 | 1/2014 | King et al. |
| 8,676,331 B2 | 3/2014 | Parker |
| 8,712,533 B2 | 4/2014 | Alataris et al. |
| 8,712,535 B2 | 4/2014 | Walker et al. |
| 9,295,840 B1 | 3/2016 | Thacker et al. |
| 2002/0068930 A1 | 6/2002 | Tasto et al. |
| 2002/0107553 A1 | 8/2002 | Hill et al. |
| 2002/0165586 A1 | 11/2002 | Hill et al. |
| 2003/0004549 A1 | 1/2003 | Hill et al. |
| 2003/0093134 A1 | 5/2003 | Bradley |
| 2003/0100931 A1 | 5/2003 | Mullett |
| 2003/0135248 A1 | 7/2003 | Stypulkowski |
| 2003/0153959 A1 | 8/2003 | Thacker et al. |
| 2003/0195582 A1 | 10/2003 | Mann |
| 2003/0212445 A1 | 11/2003 | Weinberg |
| 2004/0015202 A1 | 1/2004 | Chandler et al. |
| 2004/0116978 A1 | 6/2004 | Bradley |
| 2004/0138516 A1 | 7/2004 | Osorio et al. |
| 2004/0167584 A1 | 8/2004 | Carroll et al. |
| 2004/0215286 A1 | 10/2004 | Stypulkowski |
| 2005/0033381 A1 | 2/2005 | Carter et al. |
| 2005/0060001 A1 | 3/2005 | Singhal et al. |
| 2005/0060007 A1 | 3/2005 | Goetz |
| 2005/0209645 A1 | 9/2005 | Heruth et al. |
| 2005/0209655 A1 | 9/2005 | Bradley et al. |
| 2005/0245987 A1 | 11/2005 | Woods et al. |
| 2006/0111754 A1 | 5/2006 | Rezai et al. |
| 2006/0116742 A1 | 6/2006 | De Ridder |
| 2006/0135998 A1 | 6/2006 | Libbus et al. |
| 2006/0147932 A1 | 7/2006 | Davies et al. |
| 2006/0155348 A1 | 7/2006 | deCharms |

(56) References Cited

U.S. PATENT DOCUMENTS

| | | |
|---|---|---|
| 2006/0161236 A1 | 7/2006 | King |
| 2006/0195159 A1 | 8/2006 | Bradley et al. |
| 2006/0235472 A1 | 10/2006 | Goetz et al. |
| 2006/0247732 A1 | 11/2006 | Wesselink |
| 2006/0253174 A1 | 11/2006 | King |
| 2006/0253182 A1 | 11/2006 | King |
| 2006/0259079 A1 | 11/2006 | King |
| 2006/0259099 A1* | 11/2006 | Goetz ............... A61N 1/36071 607/66 |
| 2006/0293720 A1 | 12/2006 | DiLorenzo |
| 2007/0039625 A1 | 2/2007 | Heruth et al. |
| 2007/0073357 A1 | 3/2007 | Rooney et al. |
| 2007/0100378 A1 | 5/2007 | Maschino |
| 2007/0129774 A1 | 6/2007 | Bourget et al. |
| 2007/0150029 A1 | 6/2007 | Bourget et al. |
| 2007/0156207 A1 | 7/2007 | Kothandaraman et al. |
| 2007/0179579 A1 | 8/2007 | Feler et al. |
| 2007/0208394 A1 | 9/2007 | King et al. |
| 2007/0213773 A1 | 9/2007 | Hill et al. |
| 2007/0213789 A1 | 9/2007 | Nolan et al. |
| 2007/0245318 A1 | 10/2007 | Goetz et al. |
| 2007/0249968 A1 | 10/2007 | Miesel et al. |
| 2007/0255118 A1 | 11/2007 | Miesel et al. |
| 2007/0265679 A1 | 11/2007 | Bradley et al. |
| 2007/0265681 A1 | 11/2007 | Gerber et al. |
| 2007/0276450 A1 | 11/2007 | Meadows et al. |
| 2007/0276453 A1 | 11/2007 | Hill et al. |
| 2008/0015657 A1 | 1/2008 | Haefner |
| 2008/0046036 A1* | 2/2008 | King ............... A61N 1/0529 607/59 |
| 2008/0046052 A1 | 2/2008 | Werder et al. |
| 2008/0051839 A1 | 2/2008 | Libbus et al. |
| 2008/0064980 A1 | 3/2008 | Lee et al. |
| 2008/0071325 A1 | 3/2008 | Bradley |
| 2008/0103570 A1 | 5/2008 | Gerber |
| 2008/0109050 A1 | 5/2008 | John |
| 2008/0140150 A1 | 6/2008 | Zhou et al. |
| 2008/0154340 A1* | 6/2008 | Goetz ............... A61N 1/37247 607/59 |
| 2008/0183256 A1 | 7/2008 | Keacher |
| 2008/0188909 A1 | 8/2008 | Bradley |
| 2008/0215118 A1 | 9/2008 | Goetz et al. |
| 2008/0215119 A1 | 9/2008 | Woods et al. |
| 2008/0234791 A1 | 9/2008 | Arle et al. |
| 2008/0243196 A1 | 10/2008 | Libbus et al. |
| 2008/0269843 A1 | 10/2008 | Gerber et al. |
| 2008/0275529 A1 | 11/2008 | North et al. |
| 2008/0281381 A1 | 11/2008 | Gerber et al. |
| 2008/0319511 A1* | 12/2008 | Pless ............... A61B 5/0031 607/59 |
| 2009/0005833 A1 | 1/2009 | Cameron et al. |
| 2009/0018617 A1 | 1/2009 | Skelton et al. |
| 2009/0030476 A1 | 1/2009 | Hargrove |
| 2009/0054946 A1 | 2/2009 | Sommer et al. |
| 2009/0112281 A1 | 4/2009 | Miyazawa et al. |
| 2009/0112282 A1 | 4/2009 | Kast et al. |
| 2009/0125079 A1 | 5/2009 | Armstrong et al. |
| 2009/0149917 A1 | 6/2009 | Whitehurst et al. |
| 2009/0204173 A1 | 8/2009 | Fang et al. |
| 2009/0264956 A1* | 10/2009 | Rise ............... A61B 5/4836 607/45 |
| 2009/0264957 A1* | 10/2009 | Giftakis ............ A61M 5/14276 607/45 |
| 2009/0264967 A1* | 10/2009 | Giftakis ............ A61N 1/36082 607/62 |
| 2009/0281594 A1 | 11/2009 | King et al. |
| 2009/0281595 A1 | 11/2009 | King et al. |
| 2009/0281596 A1 | 11/2009 | King et al. |
| 2009/0281599 A1 | 11/2009 | Thacker et al. |
| 2009/0306740 A1 | 12/2009 | Heruth et al. |
| 2009/0306746 A1 | 12/2009 | Blischak |
| 2009/0326608 A1 | 12/2009 | Huynh et al. |
| 2010/0010566 A1 | 1/2010 | Thacker et al. |
| 2010/0049280 A1 | 2/2010 | Goetz |
| 2010/0057162 A1 | 3/2010 | Moffitt et al. |
| 2010/0069993 A1 | 3/2010 | Greenspan |
| 2010/0121408 A1* | 5/2010 | Imran ............... A61N 1/36071 607/46 |
| 2010/0121409 A1 | 5/2010 | Kothandaraman et al. |
| 2010/0125314 A1 | 5/2010 | Bradley et al. |
| 2010/0131034 A1 | 5/2010 | Gliner et al. |
| 2010/0137944 A1 | 6/2010 | Zhu |
| 2010/0185256 A1 | 7/2010 | Hulvershorn |
| 2010/0211135 A1 | 8/2010 | Caparso et al. |
| 2010/0228325 A1 | 9/2010 | Moffitt et al. |
| 2010/0234912 A1 | 9/2010 | Ternes et al. |
| 2010/0274312 A1 | 10/2010 | Alataris et al. |
| 2010/0274314 A1 | 10/2010 | Alataris et al. |
| 2010/0274317 A1 | 10/2010 | Parker et al. |
| 2010/0274320 A1 | 10/2010 | Torgerson |
| 2010/0274336 A1 | 10/2010 | Nguyen-Stella et al. |
| 2010/0305631 A1 | 12/2010 | Bradley et al. |
| 2010/0305660 A1 | 12/2010 | Hegi et al. |
| 2010/0312319 A1 | 12/2010 | Barker |
| 2011/0009927 A1 | 1/2011 | Parker et al. |
| 2011/0022141 A1 | 1/2011 | Chen et al. |
| 2011/0029040 A1 | 2/2011 | Walker et al. |
| 2011/0040348 A1 | 2/2011 | Wacnik et al. |
| 2011/0040351 A1 | 2/2011 | Butson et al. |
| 2011/0046697 A1 | 2/2011 | Gerber et al. |
| 2011/0054565 A1 | 3/2011 | Wacnik et al. |
| 2011/0071593 A1 | 3/2011 | Parker et al. |
| 2011/0087309 A1 | 4/2011 | Stypulkowski |
| 2011/0093051 A1 | 4/2011 | Davis et al. |
| 2011/0118661 A1 | 5/2011 | Pless et al. |
| 2011/0184488 A1* | 7/2011 | De Ridder ......... A61N 1/36071 607/46 |
| 2012/0083857 A1 | 4/2012 | Bradley et al. |
| 2012/0116476 A1 | 5/2012 | Kothandaraman |
| 2012/0130448 A1 | 5/2012 | Woods et al. |
| 2012/0172946 A1 | 7/2012 | Alataris et al. |
| 2012/0253422 A1 | 10/2012 | Thacker et al. |
| 2012/0265268 A1 | 10/2012 | Blum et al. |
| 2012/0265271 A1 | 10/2012 | Goetz |
| 2012/0310299 A1* | 12/2012 | Kaula et al. ............ 607/46 |
| 2013/0023950 A1 | 1/2013 | Gauthier |
| 2013/0060302 A1 | 3/2013 | Polefko et al. |
| 2013/0066411 A1 | 3/2013 | Thacker et al. |
| 2013/0116754 A1 | 5/2013 | Sharma et al. |
| 2013/0261694 A1 | 10/2013 | Caparso et al. |
| 2013/0310892 A1 | 11/2013 | Parker et al. |
| 2014/0081349 A1 | 3/2014 | Lee et al. |
| 2014/0330338 A1 | 11/2014 | Walker et al. |
| 2015/0217113 A1 | 8/2015 | Walker et al. |

FOREIGN PATENT DOCUMENTS

| | | |
|---|---|---|
| JP | 20020527159 | 8/2002 |
| JP | 2006502811 A | 1/2006 |
| JP | 2006212458 A | 8/2006 |
| JP | 2008526299 A | 7/2008 |
| JP | 2008534168 A | 8/2008 |
| JP | 2009519771 A | 5/2009 |
| WO | WO-0245791 A2 | 6/2002 |
| WO | WO-02096512 A1 | 12/2002 |
| WO | WO-2004098698 A2 | 11/2004 |
| WO | WO-2006119046 A1 | 11/2006 |
| WO | WO-2007149018 A1 | 12/2007 |
| WO | WO-2008142402 A1 | 11/2008 |
| WO | WO-2008157182 A1 | 12/2008 |

OTHER PUBLICATIONS

Keuchmann C et al., "853 Could Automatic Position Adaptive Stimulation be Useful in Spinal Cord Stimulation," Abstract, Medtronic, Inc., undated, 1 page.

Notice of Opposition to a European Patent for European Patent No. 2043589, Proprietor of the Patent: Nevro Corporation; Opponent: Boston Scientific Neuromodulation Corporation, Oct. 22, 2014, 32 pages.

(56) References Cited

OTHER PUBLICATIONS

Notice of Opposition to a European Patent for European Patent No. 2043589, Proprietor of the Patent: Nevro Corporation, Opponent: Medtronic, Inc., Oct. 13, 2014, 20 pages.
Walsh, Fergus, "Hope over pain relief implant which uses Wii technology," BBC New Health, http://www.bbc.co.uk/news/10509063, accessed Jul. 14, 2010, 3 pages.
U.S. Appl. No. 14/161,554, Jan. 22, 2014, Thacker et al.
U.S. Appl. No. 14/161,592, Jan. 22, 2014, Thacker et al.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
North et al., "Spinal Cord Stimulation for Axial Low Back Pain," SPINE, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Notice of Opposition to a European Patent, Argument and Facts, for European Patent No. 2459271, Proprietor of the Patent: Nevro Corporation; Opponent: Boston Scientific Neuromodulation Corporation, Jan. 20, 2016, 22 pages.

\* cited by examiner

SYSTEMS AND METHODS FOR SYSTEMATICALLY TESTING A PLURALITY OF THERAPY PROGRAMS IN PATIENT THERAPY DEVICES

CROSS-REFERENCE TO RELATED APPLICATIONS

The present application claims the benefit of U.S. Provisional Application No. 61/755,380, filed Jan. 22, 2013, the disclosure of which is hereby incorporated by reference in its entirety. The present application is related to U.S. patent application Ser. No. 14/161,554, filed Jan. 22, 2014 and U.S. patent application Ser. No. 14/161,592, filed Jan. 22, 2015, the disclosures of which are hereby incorporated by reference in their entireties. To the extent the forgoing materials and/or any other materials incorporated herein by reference conflict with the present disclosure, the present disclosure controls.

TECHNICAL FIELD

The present disclosure is directed generally to implantable neurological stimulation systems. More specifically, the disclosure is directed to methods for systematically testing a plurality of therapy programs in spinal cord stimulation systems that do not use paresthesia to mask or cover a patient's sensation of pain.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS for the treatment of pain, the signal generator applies electrical pulses to the spinal cord via the electrodes. In conventional SCS, "low frequency" electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation. Recently, a form of "high frequency" SCS has been developed, wherein high frequency electrical pulses are delivered to the spinal cord and are able to treat the patient's sensation of pain without generating paresthesia or otherwise using paresthesia to mask the patient's sensation of pain.

Both conventional SCS and high frequency SCS use a test (or "trial") period during which the most effective combination of parameters (or "program") for treating the patient's symptoms is determined. Currently, trials are conducted with a clinician placing a plurality of therapy programs in the patients' trial system. Patients then test these programs on their own during the trial period by switching between the programs. When a patient returns to the clinic, the clinician cross-references the patient's pain relief feedback against the stimulator's diagnostics. This approach can be prone to errors, and accordingly there remains a need for improved systems to efficiently identify optimal treatment programs.

SUMMARY

Disclosed herein are methods for systematically testing a plurality of therapy programs in a spinal cord stimulation system signal generator. Systematically testing the therapy programs can significantly reduce the service burden on practitioners who administer SCS therapy to patients. In a representative embodiment, the method comprises loading a plurality of therapy programs into a signal generator, wherein individual therapy programs include parameters specifying electrode configuration, signal amplitude, and/or signal frequency. The plurality of therapy programs are automatically activated for a pre-set period of time. Pre-set periods of time may range from several hours to several days (e.g., in one embodiment pre-set periods of time include 24-72 hours). The method includes automatically changing from one therapy program to another after the pre-set period of time. The patient is then queried for patient input corresponding to at least one of the plurality of therapy programs. The patient input is received via a remote device, wherein the patient input includes data representative of a level of pain relief. The patient input is then correlated with a corresponding time of day and/or therapy program, and recorded in the signal generator or remote device. Thereafter, the patient input may be retrieved from the signal generator for further analysis. In some embodiments, other informative data can be collected and recorded in the signal generator or remote device (e.g., positional data via an accelerometer). In particular embodiments, automatically activating the therapy programs can improve the accuracy of the process by ensuring that the patient tries each tested program for a sufficient period of time, even if the patient is not receiving sensory feedback (in the form of paresthesia) to indicate that the program is active. Furthermore, the automatic activation process can reduce the work load on the practitioner and/or the patient.

DETAILED DESCRIPTION

Figure 1:
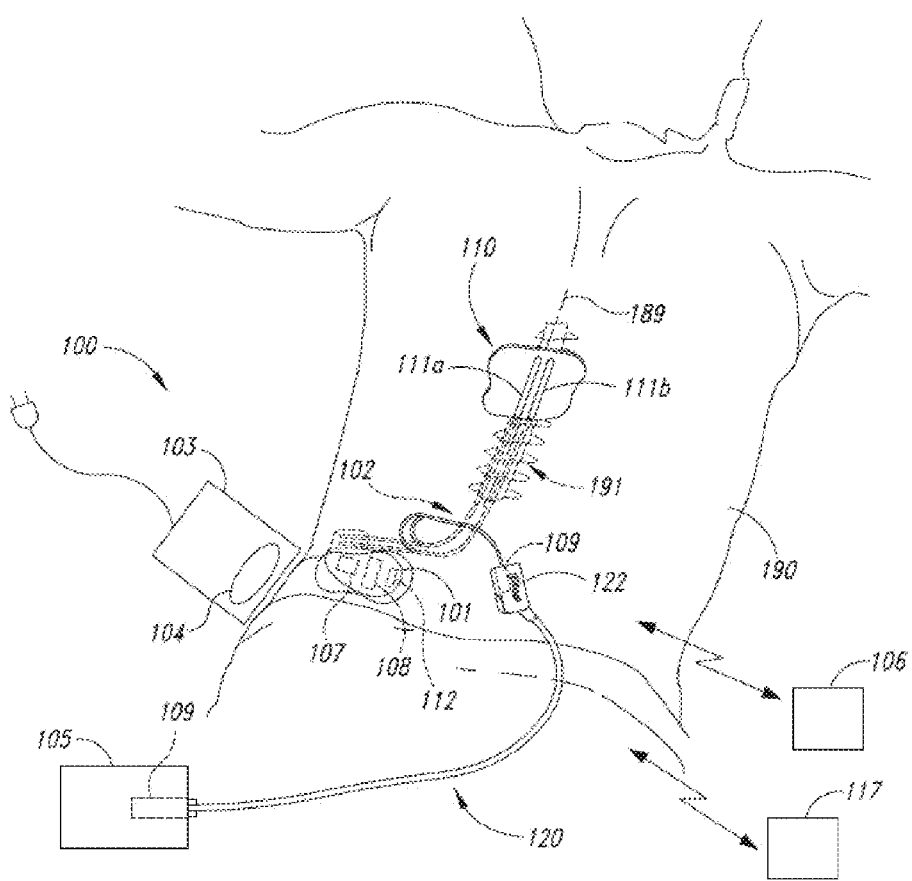
FIG. 1 is a partially schematic illustration of an implantable spinal cord stimulation system positioned at the spine to deliver therapeutic signals in accordance with several embodiments of the present disclosure.

The present technology is directed generally to systematically testing a plurality of therapy programs in patient therapy systems, such as spinal cord stimulation (SCS) systems. For example, in one embodiment, the present technology is employed in SCS systems that provide pain relief without generating paresthesia.

"High frequency" SCS systems, for example, inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.5 kHz to about 100 kHz) is occasionally referred to herein as high frequency modulation.

As mentioned above, high frequency SCS therapy has recently been determined to provide therapy without generating paresthesia or unwanted pain or other sensory or motor effects. Accordingly, high frequency SCS therapy may be applied over a large area without the need to determine which pair(s) of contacts provide the appropriate paresthesia to cover or mask a patient's area of pain (a procedure commonly referred to as "paresthesia mapping" in conventional SCS therapy). However, because high frequency SCS (and other paresthesia-free pain therapy systems) do not provide the tangible and immediate feedback present with paresthesia-based SCS systems, finding the optimal program parameters for paresthesia-fee SCS systems may be difficult.

Several embodiments described herein provide a systematic approach for sequentially activating therapy programs provided by a signal generator in paresthesia-free SCS systems. Specific details of certain embodiments of the disclosure are described below with reference to methods for modulating one or more target neural populations (e.g., nerves) or sites of a patient, and associated implantable structures for providing the modulation. Although selected embodiments are described below with reference to modulating the dorsal column, dorsal horn, dorsal root, dorsal root entry zone, and/or other particular regions of the spinal column to control pain, the modulation may in some instances be directed to other neurological structures and/or target neural populations of the spinal cord and/or other neurological tissues. Some embodiments can have configurations, components, or procedures different than those described in this section, and other embodiments may eliminate particular components or procedures. Accordingly, the disclosure may encompass other embodiments with additional elements and/or steps and may include other embodiments without several of the features or steps shown and described below with reference to FIGS. 1-3.

While the systems and methods described herein are applicable to all paresthesia-free therapy systems, aspects of many of the following embodiments are described as systematically testing a plurality of therapy programs in order to find the most effective program for high frequency SCS systems. Such descriptions are meant to be examples, and are not meant to be limiting. In other words, although the representative embodiments are described herein with respect to a high frequency SCS system, the methods may be applicable in at least some embodiments to certain types of low frequency SCS systems, as well as other therapy systems for treatment of pain or other conditions.

The techniques described below with reference to FIGS. 1-3 can provide a system that automatically activates various therapy programs loaded into a signal generator or remote device. The system can automatically query the patient to enter his/her pain level using a remote or other capture device, such as a mobile device. In addition, the patient can voluntarily enter his/her pain level at any time. The system may be overridden by the patient to either turn off or "dwell" on any program. The provided system and methods help to ensure that the therapy programs have each been suitably tested.

FIG. 1 schematically illustrates a representative patient therapy system 100 for providing relief from chronic pain and/or other conditions, arranged relative to the general anatomy of a patient's spinal column 191. The system 100 can include a signal generator 101 (e.g., a pulse generator), which may be implanted subcutaneously within a patient 190 and coupled to one or more signal delivery elements or devices 110. The signal delivery elements or devices 110 may be implanted within a patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms lead and lead body include any of a number of suitable substrates and/or support members that carry devices for providing therapy signals to the patient 190. For example, the lead or leads 111 can include one or more electrodes or electrical contacts 115 (see FIGS. 2A and 2B) that direct electrical signals into the patient's tissue, such as to provide for patient pain relief. In other embodiments, the signal delivery elements 110 can include structures other than a lead body (e.g., a paddle) that also direct electrical signals and/or other types of signals to the patient 190.

One device may be implanted on one side of the spinal cord midline 189, and a second device may be implanted on the other side of the spinal cord midline 189. Leads 111a, 111b (see FIGS. 2A and 2B) may be positioned just off the spinal cord midline 189 (e.g., about 1 mm. offset) in opposing lateral directions so that the two leads 111a, 111b are spaced apart from each other by about 2 mm. In particular embodiments, the leads 111 may be implanted at a vertebral level ranging from, for example, about T8 to about T12. In other embodiments, one or more signal delivery devices can be implanted at other vertebral levels, e.g., as disclosed in U.S. pending application Ser. No. 13/607,617, now published as U.S Patent Application Publication No. 2013/0066411 filed on Sep. 7, 2012, incorporated herein by reference in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, and/or executing other associated functions can be performed by computer-executable instructions contained by computer-readable media located at the pulse generator 101 and/or other system components. The signal generator 101 can include multiple portions, elements, and/or subsystems (e.g., for directing signals in accordance with multiple signal delivery parameters), carried in a single housing, as shown in FIG. 1, or in multiple housings.

The signal generator 101 can also receive and respond to an input signal received from one or more sources. The input signals can direct or influence the manner in which the therapy instructions are selected, executed, updated, and/or otherwise performed. The input signal can be received from one or more sensors 112 (one is shown schematically in FIG. 1 for purposes of illustration) that are carried by the signal generator 101 and/or distributed outside the signal generator 101 (e.g., at other patient locations) while still communicating with the signal generator 101. The sensors 112 can provide inputs that depend on or reflect patient state (e.g., patient position, patient posture, and/or patient activity level), and/or inputs that are patient-independent (e.g., time). Still further details are included in co-pending U.S. application Ser. No. 12/703,683, now issued as U.S. Pat. No. 8,355,797, filed on Feb. 10, 2010 and incorporated herein by reference in its entirety.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use. In one embodiment, external power source 103 can by-pass an implanted signal generator and generate a therapy signal directly at the signal delivery device 110 (or via signal relay components).

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. Receiving elements 109 can be at least generally similar in structure and function to those described in U.S. patent application Ser. No. 13/291,985, now published as U.S. Patent Application Publication No. 2013/0116754, entitled MEDICAL DEVICE CONTACT ASSEMBLIES FOR USE WITH IMPLANTABLE LEADS, AND ASSOCIATED SYSTEMS AND METHODS, filed Nov. 8, 2011, which is incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals, which can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. Certain aspects of the foregoing systems and methods may be simplified or eliminated in particular embodiments of the present disclosure. Further aspects of these and other expected beneficial results are detailed in co-pending U.S. application Ser. No. 12/765,810, now published as U.S. Patent Application Publication No. 2010/0274317, filed on Apr. 22, 2010; U.S. patent application Ser. No. 12/765,747, now issued as U.S. Pat. No. 8,712,533, filed Apr. 22, 2010; and U.S. patent application Ser. No. 12/264,836, now published as U.S. Patent Application Publication No. 2009/0204173, filed Nov. 4, 2008, all of which are incorporated herein by reference in their entireties.

Given the multitude of parameters that may be varied in SCS therapy, there are many possible combinations of parameters for therapy programs. Each candidate therapy program must be tested for a period of time to determine its efficacy. It has been found that, for some patients, high frequency SCS does not produce effective therapy immediately. This may be the result of hysteresis or a similar response characteristic, and is unlike conventional, paresthesia-based SCS, which immediately causes paresthesia and immediately provides the patient and practitioner with feedback as to whether the conventional SCS therapy will ultimately be effective for that particular patient. In many cases, the delay in effectiveness for high frequency SCS can range from about 20 minutes to about 48 hours. Accordingly, it can take a significant amount of time to adequately test all of the desired therapy program parameter combinations for high frequency SCS therapy.

Rather than having the patient remain in the clinic for all of the testing, which would be cost-prohibitive, or relying on the patient to cycle through the desired programs, the presently disclosed methods provide a process for automatically and systematically testing a plurality of therapy programs. Automatically cycling through the desired programs can also prevent patients from skipping programs if they do not immediately feel an effect, thereby ensuring that each program is tested long enough to determine whether it is an effective combination of parameters. It should be further appreciated that the test programs can be changed without the patient's knowledge because high frequency SCS cannot be sensed by the patient other than by the resulting pain relief. Accordingly, a placebo effect, if it exists, may be reduced. In addition, if a placebo effect is suspected for a particular program, that program can be retested without the patient's knowledge to determine whether the particular program is truly effective. For example, a patient can be queried for pain relief feedback while no program is running in order to determine if the patient believes he/she is receiving pain relief even though the system is inactive.

In some embodiments, the hysteresis delay can be measured and accounted for in the program parameters. For example, the system can initiate a program and begin querying the patient at regular intervals until pain relief is experienced and recorded by the patient, thereby measuring a pain relief onset delay. Similarly, the program can be discontinued while the patient is queried at regular intervals until pain relief fades, thereby measuring a pain relief residual delay. In particular embodiments, the measured onset delay and residual delay can be included in the program parameters in order to account for the delays and provide continuous pain relief, for example. In a representative embodiment, the system can ensure that a program under test remains active for at least as long as the onset delay, which can be predetermined, as explained above, for a particular patient and circumstances. Similarly, the system can remain inactive (i.e., without providing stimulation) for at least as long as the residual delay before activating another program.

In a representative embodiment, the clinician programs the signal generator as in a traditional system with various therapy programs. The signal generator can be implanted or external. In addition, the signal generator is programmed with a test sequence for cycling through the therapy programs. Without any intervention by the patient, the system sequences the patient through the different therapy programs (e.g., parameter sets). The system is constrained by the programs programmed into the signal generator by the clinician.

Figure 2A:
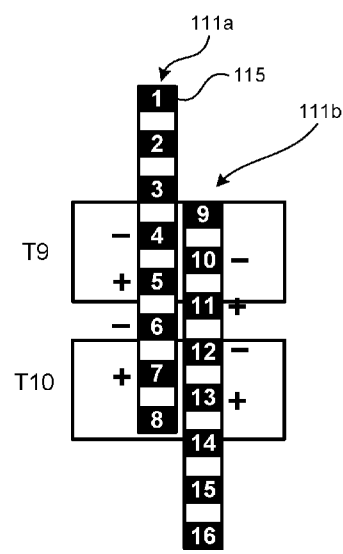
FIG. 2A is a schematic representation of two vertebrae and a representative electrode configuration.
Figure 2B:
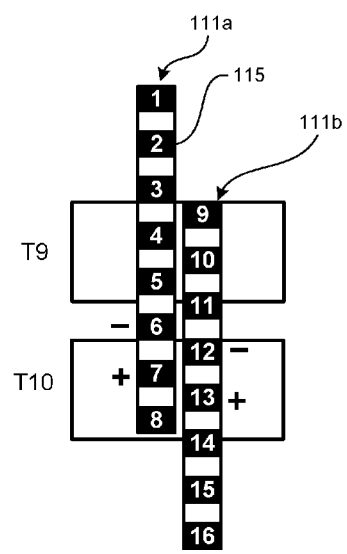
FIG. 2B is a schematic representation of two vertebrae and another representative electrode configuration.

FIGS. 2A and 2B illustrate representative examples of possible electrode configurations used in high frequency SCS therapy programs. In this example, a pair of leads 111a and 111b (collectively referred to as leads 111) are located along vertebrae T9 and T10 as shown. Each lead 111 includes eight contacts 115. Accordingly, the contacts 115 are numbered 1-16 for reference. An electrode configuration A is shown in FIG. 2A in which four anode-cathode pairs are activated. As shown, 4, 5, 6, 7, 10, 11, 12, and 13 are active in configuration A. FIG. 2B illustrates another configuration, electrode configuration B. In this configuration only two anode-cathode pairs are active. In this case, electrodes 6, 7, 12, and 13 are active. It should be understood that the lead locations with respect to T9 and T10 as well as the number of contacts, are representative, and other combinations of leads and electrode configurations may be employed in other implementations of the present technology.

As described above, the signal generator 101 may be programmed with a plurality of different therapy programs, each of which includes particular parameters, e.g., specifying electrode configuration, amplitude, frequency, and/or pulse width. Table 1 illustrates four representative programs and associated parameter values. The programs may have various combinations of parameter values which are selected by a health care provider, physician, and/or other practitioner. In this example, Programs 1-3 each specify electrode configuration A activated at a signal frequency of 10 kHz. However, in Programs 1-3 the amplitude is varied from 2.5 mA to 3.5 mA. Accordingly, by sequentially activating Programs 1-3, electrode configuration A, at a signal frequency of 10 kHz, is suitably tested over a selected range of amplitudes. Each program is automatically activated for a practitioner-selected pre-set period of time before the signal generator automatically switches to the next program. The active time for each program may be variable or fixed. Furthermore, the active time period may be a parameter that varies from one therapy program to another. The practitioner may choose the order in which to test the programs. For example, the programs may be tested in a practitioner-selected sequence (e.g., lowest to highest, highest to lowest, random, etc.).

TABLE 1

|  | Electrode Config. | Frequency | Amplitude |
| --- | --- | --- | --- |
| Program 1 | A | 10 kHz | 2.5 mA |
| Program 2 | A | 10 kHz | 3.0 mA |
| Program 3 | A | 10 kHz | 3.5 mA |
| Program 4 | B | 10 kHz | 2.5 mA |

As shown in Table 1, Program 4 changes to electrode configuration B with a signal frequency of 10 kHz and an amplitude of 2.5 mA. It should be appreciated that Table 1 is provided for illustrative purposes only and that various other electrode configurations, frequencies, and amplitudes may be specified for other programs. It should also be understood that by switching between various programs having different configurations and parameters, variations in program parameters may be suitably tested in an automatic fashion without reliance on a patient or practitioner to conduct the test. For example, Programs 1-3 suitably test the amplitude range for electrode configuration A at signal frequency of 10 kHz. In other embodiments, the parameters can be varied in other manners. For example, the amplitude step size from one program to another can be greater than or less than 0.5 mA, and/or the range can be different in an overlapping or non-overlapping manner relative to the range shown in Table 1.

Figure 3:
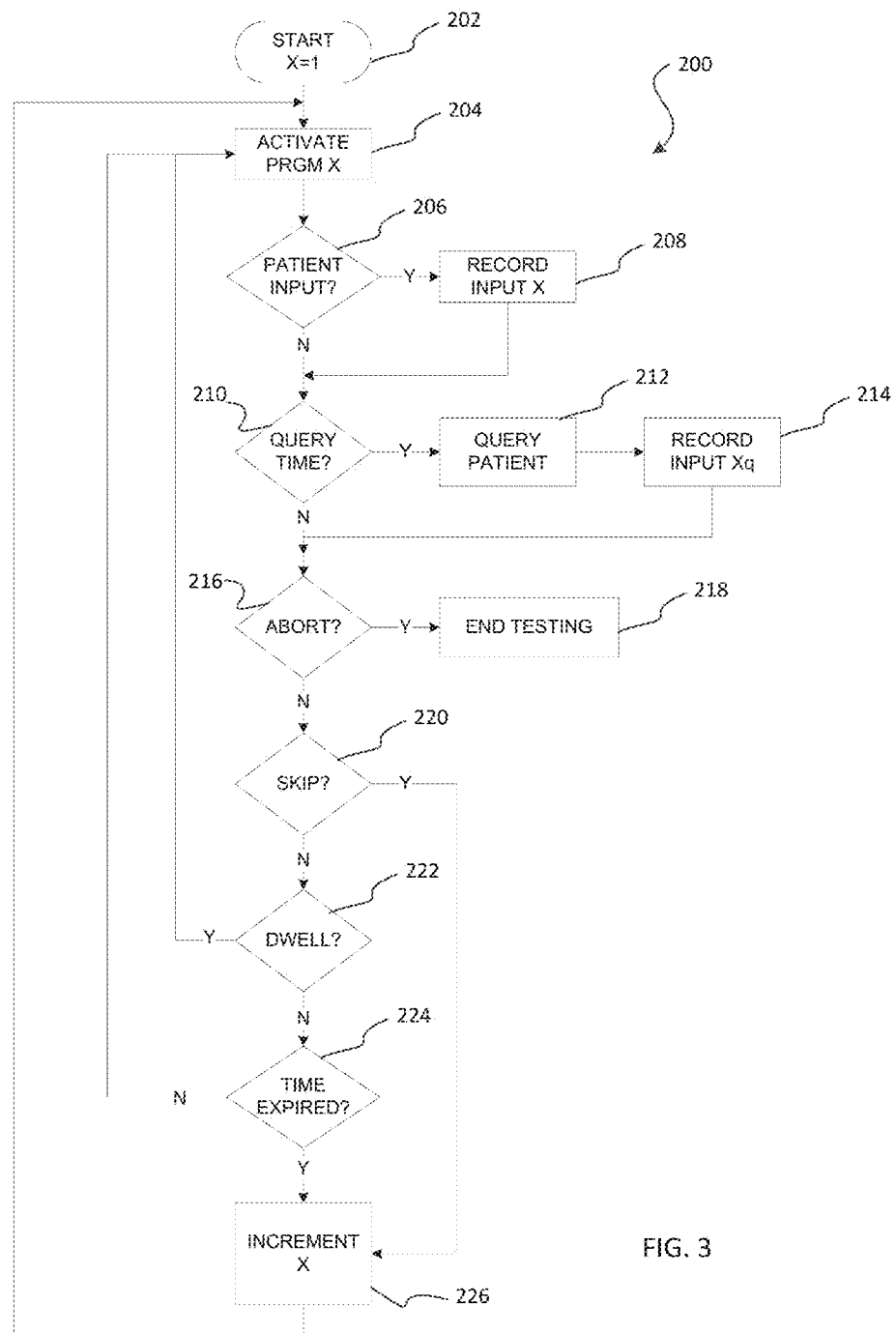
FIG. 3 is a flow diagram illustrating a method of systematically testing a plurality of therapy programs according to a representative embodiment.

FIG. 3 illustrates a method 200 for systematically testing a plurality of therapy programs X in a patient therapy system signal generator using a series of steps or process portions. Starting at step or process portion 202, X is set to 1, so that therapy Program 1 is activated at step 204. The activated program will run (e.g., loop) for a pre-set period of time unless an interrupt occurs, as described more fully below. At step 206, a patient may spontaneously decide to record an input, such as a level of efficacy, into the signal generator. The level of efficacy may be in the form of a level of pain relief, such as a Visual Analog Scale (VAS) pain score (or another suitable measure). If patient input has been received at step 206, the input is recorded at step 208 as input X.

The level of pain relief may be recorded and/or it may be used to change the program test sequence. In some embodiments, changing the program test sequence can be according to a decision algorithm based on patient input and/or sensor input. As an example, if the VAS pain score is below a threshold (e.g., 2), then the test sequence does not progress, but dwells at the current settings, e.g., the settings of program 1. In another embodiment, if the pain score increases, the process continues with the test sequence. In one implementation, the patient can use a smartphone, tablet, and/or other suitable device to enter the VAS pain score, which is then communicated to the signal generator 101 for storage and possible further action. In another implementation, the patient uses controls on the trial stimulator 105 or the patient remote 106 to log in a pain score. The system components can include a number of features that allow the patient to capture this information. For example, the patient remote may include a VAS keypad that allows the patient to select a button that reflects his/her current pain level, zero being the lowest and ten being the highest.

The signal generator may query the patient for input at step 210. For example, the signal generator may transmit a command to the patient's remote to sound an alarm indicating to the patient that input is requested. In a particular embodiment, the patient is queried after the current program has been active for a suitable period of time (e.g., 1-2 days). If a sufficient amount of time has passed at step 210, the patient is queried at step 212 and any input from the patient is recorded as queried input Xq at step 214. If the patient decides to abort the testing altogether at step 216, the testing is ended at step 218; otherwise, testing continues. If a skip input is received from the patient at step 220, the process jumps to step 226 where X is incremented in order to activate the next program. If the patient skips a program, the system can automatically track this (and other) actions. Accordingly, the system can notify the practitioner that a program was skipped, and the practitioner can take a follow-up action, e.g., asking the patient why the program was skipped, and making potential adjustments on the basis of the patient's response. If a dwell input is received from the patient at step 222, the process jumps to step 204 where the current program remains activated. Whether the abort, skip, and/or dwell features are available to the patient may be controlled by the clinician. In some embodiments, the clinician can intervene remotely to skip, dwell, or abort, for example. In other embodiments, an in-home monitor can interrogate the signal generator to download parameter information and patient input for communication to the clinician. In a further embodiment, the in-home monitor can change the programs as necessary.

Each therapy Program X is activated for a pre-set period of time, e.g., a practitioner-selected pre-set period of time. As such, a determination at step 224 is made as to whether that time period has expired. If the time period has expired, X is incremented at step 226, and the process returns to step 204 where the next program is activated. Accordingly, programs (e.g., the first program and/or subsequent programs) can be activated automatically, without human intervention. Otherwise, if time has not expired, the process returns (e.g., loops) to step 204 where the current program continues to run.

Certain of the foregoing embodiments can produce one or more of a variety of advantages, for the patient and/or the practitioner, when compared with traditional techniques. Some of these benefits were described above. For example, the disclosed systems and methods can help to ensure that the therapy programs are suitably tested to efficiently and conveniently determine the most effective program to provide pain relief to a patient.

Another feature of embodiments of the foregoing technology is that rather than having the patient remain in the clinic for all of the testing, or relying on the patient to cycle through the desired programs on his/her own, the disclosed technology sequences the patient through the different therapy programs (e.g., parameter sets) automatically. Thus, the patient can go about a somewhat normal routine while the system automatically tests the various programs, all without reliance on the patient to remember which parameters have been tested and which need further testing. Furthermore, important patient input is automatically elicited and correlated to the program being tested and the time of day for later analysis or real-time adjustments.

Normally, activating all or many of the electrodes simultaneously can consume a significant amount of power. This is not typically a problem with the battery capacity of a trial modulator. However, with an implanted signal generator it is desirable to limit the number of contacts that are activated in order to conserve battery life. High frequency SCS therapy has also recently been determined to deliver effective therapy at relatively low duty cycles when compared to conventional SCS therapy. Thus, a large area of high frequency SCS therapy coverage may be achieved with acceptable power consumption by activating the contacts at a lower duty cycle. Therefore, in accordance with embodiments of the present technology, effective high frequency SCS therapy may be achieved with an implanted signal generator without the need for programming optimization to select the least number of electrical contacts. Other parameters (e.g., current or voltage amplitude) may be optimized using processes including those described herein.

Provided herein are methods and systems for systematically testing a plurality of therapy programs in a patient therapy system signal generator. In a representative embodiment, the method comprises loading a plurality of therapy programs into a signal generator and automatically activating the plurality of therapy programs. The therapy programs may include parameters specifying electrode configuration, signal amplitude, and signal frequency. Individual therapy programs are activated for an automatically instructed pre-set period of time. Patient input is received corresponding to at least one of the plurality of therapy programs. In an embodiment, the method further comprises automatically changing from one program to another after the automatically instructed pre-set period of time has elapsed. In another embodiment, the patient is queried to provide the patient input.

In another representative embodiment, the method comprises loading a plurality of therapy programs into a signal generator and automatically activating the plurality of therapy programs in a sequence. The individual therapy programs are activated for an automatically instructed pre-set period of time to deliver therapy to a patient. The patient is queried for patient input corresponding to individual therapy programs. The patient input is recorded in the signal generator for corresponding individual therapy programs. The patient inputs are retrieved from the signal generator.

In another embodiment, a spinal cord stimulation system comprises a signal generator having (e.g., before and/or after implantation) a plurality of therapy programs. The signal generator can be external to or implantable in the patient. The signal generator is operable to automatically activate the plurality of therapy programs in a sequence for an automatically instructed pre-set period of time. A patient remote is operable to query the patient for patient input corresponding to individual therapy programs. At least one memory unit is operable to record the patient input. In a particular embodiment, the system further comprises a practitioner remote operable to retrieve the patient input from the at least one memory unit. In another embodiment, the sequence is selected by a practitioner via the practitioner remote. In one aspect of the disclosed technology, the patient remote is operable to communicate with the signal generator. In another aspect of the technology, the at least one memory unit is housed in the signal generator.

In one aspect of the present technology described herein, the patient input includes a dwell input indicating the patient wishes to dwell on a currently active program. In another aspect of the present technology, the patient input includes an abort input indicating the patient wishes to abort the testing. In yet another aspect of the technology, the patient input includes a skip input indicating the patient wishes to skip a currently active program.

In other aspects of the present technology, the automatically instructed pre-set period of time is not patient selected. In some embodiments, the sequence is practitioner selected. Individual patient inputs are correlated with a corresponding program and may be correlated with a corresponding time of day. In another aspect of the disclosed technology, the patient input includes a level of efficacy of the therapy program, such as a level of pain relief. In some embodiments, the patient input is received via a mobile device.

In a particular embodiment, any one or more of the above-described paresthesia-free modulation therapies may be applied at specific duty cycles that have shown superior results over large population pools. For example, the therapy signal can be applied at duty cycles wherein the modulation is on for a period of from about 1 msec. to about 2 seconds, and off for a period of from about 1 msec. to about 1.5 seconds. In other embodiments, longer on and off time periods have also produced superior results. For example, in a representative embodiment, the high frequency modulation signal can be on for approximately 20 seconds and off for approximately 120 seconds. In another embodiment, the high frequency modulation signal can be on for 10-20 seconds and off for 60-120 seconds. In a particular embodiment, the stimulation may be applied generally at a duty cycle of around 10%.

In certain embodiments the amplitude of the therapy signal can range from about 0.1 mA to about 20 mA, or from about 0.5 mA to about 10 mA, or from about 0.5 mA to about 4 mA, or from about 0.5 mA to about 2.5 mA. The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,836, now published as U.S. Patent Application Publication No. 2009/0204173, incorporated herein by reference.

In certain embodiments, the pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds.

In some embodiments, applying a short pulse width waveform via the signal generator and the signal delivery device is effective in providing pain relief without generating paresthesia. Many such examples are described herein in the context of high frequency signals (e.g., signals with a frequency of 1.5 kHz to 100 kHz). In other embodiments, the signals can have short pulse widths, at high or low frequencies. In particular examples, the signal (or at least a portion of the signal) can have pulses with pulse widths ranging from about 10-50 microseconds, or from about 20-40 microseconds, or from about 25-35 microseconds, or from about 30-35 microseconds, or about 30 microseconds. The amplitude of the waveform (e.g., the amplitudes of the individual pulses) can be from about 0.5-20 mA, or from about 2-18 mA, or from about 5-15 mA, or from about 7-10 mA, or about 0.5-7 mA. Meanwhile, the frequency of the therapy signal (or at least a portion of the signal) can be at or below 1.5 kHz, e.g., from about 2 Hz to about 1.5 kHz, or from about 500 Hz to about 1.5 kHz, or from about 700 Hz to about 1.5 kHz, or from about 1 kHz to about 1.5 kHz, or about 1.2 kHz. In one representative example, the therapy signal includes a frequency of 1,200 Hz, a pulse width of 30 microseconds, and an amplitude that provides pain relief without generating paresthesia (generally between 0.5-20 mA).

In any of the foregoing embodiments, aspects of the therapy provided to the patient may be varied within or outside the representative parameters described above, while still obtaining beneficial results for patients suffering from chronic pain and/or other indications. For example, the location of the signal delivery device (and in particular, the signal delivery device electrical contacts or electrodes) can be varied over the significant lateral and/or axial ranges.

The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in particular embodiments, the signal amplitude refers to the electrical current level, e.g., for current-controlled systems. In other embodiments, the signal amplitude can refer to the electrical voltage level, e.g., for voltage-controlled systems. In cases for which the signal generator includes a constant voltage arrangement rather than a constant current arrangement, the current values described above may be replaced with corresponding voltage values.

Many embodiments of the technology described above may take the form of computer-executable instructions, including routines executed by a programmable computer. Those skilled in the relevant art will appreciate that the technology can be practiced on computer systems other than those shown and described below. The technology can be embodied in a special-purpose computer or data processor that is specifically programmed, configured or constructed to perform one or more of the computer-executable instructions described below. Accordingly, the term "computer" or "controller" as generally used herein refers to any data processor and can include Internet appliances and hand-held devices (including palm-top computers, wearable computers, cellular or mobile phones, multi-processor systems, processor-based or programmable consumer electronics, network computers, mini computers and the like). Information handled by these computers can be presented at any suitable display medium, including a CRT display or LCD.

The technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on computer-readable media, including magnetic or optically readable or removable computer disks, as well as distributed electronically over networks. In particular embodiments, data structures and transmissions of data particular to aspects of the technology are also encompassed within the scope of the technology.

From the foregoing, it will be appreciated that specific embodiments of the disclosed technology have been described herein for purposes of illustration, but that various modifications may be made without deviating from the technology. For example, patient input can be recorded at or by the signal generator in some embodiments, and/or by other system components in other embodiments. Suitable components include a patient remote, handwritten notes, a separate patient device (e.g., a smartphone or computer), among others.

Certain aspects of the disclosure described in the context of particular embodiments may be combined or eliminated in other embodiments. For example, in some embodiments the patient may have the option to skip a program, and in others, the option may be eliminated or limited. In another example, each program may specify signal amplitude and electrode identity, and other program parameters (e.g., frequency and pulse width) can default to pre-set values that remain the same across multiple programs. Therapies directed to particular indications may be combined in still further embodiments. Additional indicators are disclosed in pending U.S. application Ser. No. 13/607,617, now published as U.S Patent Application Publication No. 2013/0066411, previously incorporated herein by reference. Further, while advantages associated with certain embodiments have been described in the context of those embodiments, other embodiments may also exhibit such advantages, and not all embodiments need necessarily exhibit such advantages to fall within the scope of the present disclosure.

Accordingly, the present disclosure and associated technology can encompass other embodiments not expressly shown or described herein.

We claim:

1. A spinal cord stimulation system, comprising:
   a signal generator having a plurality therapy programs, wherein the signal generator is operable to determine an onset delay period between initiation of a therapy signal and onset of pain relief and automatically activate individual therapy programs in a sequence, each for longer than the onset delay period;
   a patient remote operable to query the patient for patient input corresponding to individual therapy programs; and
   at least one memory unit operable to record the patient input.

2. The system of claim 1, wherein the patient remote is operable to communicate with the signal generator.

3. The system of claim 1, wherein the at least one memory unit is housed in the signal generator.

4. The system of claim 1, further comprising a practitioner remote operable to retrieve the patient input from the at least one memory unit.

5. The system of claim 4, wherein the sequence is selected by a practitioner via the practitioner remote.

6. The system of claim 1, wherein the signal generator is operable to automatically turn off one therapy program in the sequence and automatically initiate a second therapy program in the sequence after a residual delay period in which no therapy program is active.

7. A method for systematically testing a plurality of therapy programs in a patient therapy system signal generator, the method comprising:
   loading a plurality of therapy programs into a patient therapy system signal generator;
   determining an onset delay period corresponding to a delay between initiation of a therapy signal and onset of pain relief;
   automatically activating the plurality of therapy programs, wherein individual therapy programs are activated without human intervention, for longer than the onset delay period; and
   receiving patient input corresponding to at least one of the plurality of therapy programs.

8. The method of claim 7, further comprising automatically turning off one therapy program and automatically initiating a second therapy program after a residual delay period.

9. The method of claim 7, further comprising querying a patient for the patient input.

10. The method of claim 7, wherein the patient input is correlated with a corresponding program.

11. The method of claim 10, wherein the patient input is correlated with a corresponding time of day.

12. The method of claim 7, wherein the patient input includes a level of efficacy of the therapy program.

13. The method of claim 12, wherein the level of efficacy corresponds to a level of pain relief.

14. The method of claim 7, wherein the patient input is received via a mobile device.

15. A method for systematically testing a plurality of therapy programs in a spinal cord modulation system signal generator, the method comprising:
   loading a plurality of therapy programs into a spinal cord modulation system signal generator, wherein the therapy programs deliver paresthesia-free therapy;

determining an onset delay period corresponding to a delay between initiation of a therapy signal and onset of pain relief;
automatically activating the plurality of therapy programs in a sequence, wherein individual therapy programs are activated for longer than the onset delay period;
querying the patient for patient input corresponding to individual therapy programs;
recording the patient input corresponding to the individual therapy programs in the spinal cord modulation system signal generator; and
retrieving the patient input from the spinal cord modulation system signal generator.

16. The method of claim 15, wherein the patient input is correlated with a corresponding program.

17. The method of claim 15, wherein the patient input includes a level of efficacy of the therapy program.

18. The method of claim 17, wherein the level of efficacy corresponds to a level of pain relief.

19. The method of claim 15, wherein individual therapy programs include parameters specifying electrode configuration, signal amplitude, and signal frequency.

20. The method of claim 15, wherein the sequence is practitioner selected.

21. The method of claim 15, further comprising automatically turning off one therapy program in the sequence and automatically initiating a second therapy program in the sequence after a residual delay period in which no therapy program is active.

22. A method for systematically testing a plurality of therapy programs in a spinal cord modulation system signal generator, the method comprising:
loading a plurality of paresthesia-free therapy programs into a spinal cord modulation system signal generator, wherein individual therapy programs include parameters specifying electrode configuration, signal amplitude, and signal frequency;
determining an onset delay period corresponding to a delay between initiation of a therapy signal and onset of pain relief;
automatically activating the plurality of therapy programs, wherein individual therapy programs are activated sequentially for at least as long as the onset delay period;
automatically changing from one therapy program to another after the onset delay period;
querying a patient for patient input corresponding to at least one of the plurality of therapy programs;
receiving the patient input via a remote, wherein the patient input includes a level of pain relief;
correlating the patient input with a corresponding time of day;
recording the patient input in the spinal cord modulation system signal generator; and
retrieving the patient input from the spinal cord modulation system signal generator.

23. The method of claim 22, wherein the patient input includes a dwell input indicating the patient wishes to dwell on a currently active program.

24. The method of claim 22, wherein the patient input includes an abort input indicating the patient wishes to abort the testing.

25. The method of claim 22, wherein the patient input includes a skip input indicating the patient wishes to skip a currently active program.

* * * * *